United States Patent [19]

Dietrich et al.

[11] Patent Number: 5,965,135
[45] Date of Patent: *Oct. 12, 1999

[54] HIV-1 VIRUS ISOLATES OF A SUBTYPE AND ITS DIFFERENTIAL DIAGNOSTICS

[75] Inventors: Ursula Dietrich, Eschborn; Hagen Von Briesen, Hunstetten; Manuel Grez, Dossenheim; Helga Rubsamen-Waigmann, Bad Soden, all of Germany

[73] Assignee: Chemotherapeutisches Forschungsinstitut, Frankfurt, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/392,806

[22] PCT Filed: Aug. 25, 1993

[86] PCT No.: PCT/EP93/02275

§ 371 Date: Apr. 20, 1995

§ 102(e) Date: Apr. 20, 1995

[87] PCT Pub. No.: WO94/05327

PCT Pub. Date: Mar. 17, 1994

[30] Foreign Application Priority Data

Aug. 29, 1992 [DE] Germany ............... 42 28 787

[51] Int. Cl.⁶ .......... A61K 39/21; A61K 39/38; C07K 14/00; C07K 1/00
[52] U.S. Cl. .......... 424/188.1; 424/184.1; 424/208.1; 530/395; 530/350; 435/5; 435/7.1; 435/7.2
[58] Field of Search ........... 424/188.1, 208.1, 424/184.1; 435/7.1, 7.2, 5; 530/395, 350

[56] References Cited

U.S. PATENT DOCUMENTS 5,030,449  7/1991  Berzofsky et al. .......... 424/88
5,128,319  7/1992  Arlinghaus .............. 514/12
5,576,000  11/1996  Reitz et al. ............ 424/188.1

FOREIGN PATENT DOCUMENTS 0 498 905   8/1982   European Pat. Off. .
0 327 180   8/1989   European Pat. Off. .
WO 88/10267 12/1988  WIPO .
WO 92/05800  4/1992  WIPO .

OTHER PUBLICATIONS

International Search Report, PCT/EP 93/ 02275, Feb. 11, 1994.

International Preliminary Examination Report, PCT/EP 93/02275, Dec. 9, 1994.

Cohen, J: Jitters Jeopardize AIDS Vaccine Trials: Science vol. 262: pp. 980–981: 1993.

Pietrich, V., et al: Detection of Highly Divergent HIV Strains on India: Int. Conf. AIDS(Netherlands): 8(a) pH:12: Abstract BAQ 2095:1992.

Dietrich, et al. : Detection of highly divergent HIV strains in India: Int. Conf. AIDS: 8(2): pA12 (abstract No. PoA 2055).

*Primary Examiner*—Frank C. Eisenschenk
*Assistant Examiner*—Brett Nelson
*Attorney, Agent, or Firm*—Jacobson, Price, Holman & Stern, PLLC

[57] ABSTRACT

Three new HIV-1 isolates HIV-1 D747(ECACC V92082718), HIV-1 D757(ECACC V92082719) and HIV-1 D760(ECACC V92082720) are disclosed, which represent a further independent subtype of the HIV-1 family and have been recovered from Indian patients which at the time when the virus was isolated showed no typical AIDS symptoms. Also disclosed are vaccines against HIV-1 infections by this subtype and a process for producing the same, as well as the use of the HIV-1 infection, as well as for differential diagnosis.

4 Claims, No Drawings

HIV-1 VIRUS ISOLATES OF A SUBTYPE AND ITS DIFFERENTIAL DIAGNOSTICS

This application is a 371 of PCT/EP93/02275 filed on Aug. 25, 1993.

The invention relates to new HIV-1 virus isolates of a subtype, vaccines against HIV-1 virus infections of this subtype, methods of producing same, and the use of the virus isolates for the production of vaccines and for differential diagnostics.

Hitherto, efforts to develop agents for the prophylaxis and therapy of HIV infections have focused on the inhibition of the reverse transcriptase or some other enzyme of the HIV-1 virus such as, for example, protease. Thereby a specific inhibition of viral replication in contrast to cellular replication is intended to be accomplished. Nevertheless, the antiviral agents of prior art suffer from the drawback that they are accompanied by a relatively high toxicity towards the cells, i.e. they do not only affect the virus.

Those groups of substances which have been identified as being active against HIV viruses include, inter alia, various nucleoside analogues (azidothymidine, di-deoxyinosine and di-deoxycytidine). However, a massive formation of resistence of the virus has been detected after some relatively short periods of therapy with these substances {Zimmermann et al., Abstract No. 3656, IV International Conference on AIDS, Stockholm, 1988, R übsamen-Waigmann et al., Infection 19, Suppl. 2, 77–82, 1991}. Furthermore, all of the substances mentioned produce considerable side-effects, at least when applied in higher doses.

Another inhibitor of reverse transcriptase is the substance Suramin. However, this substance, due to its toxicity towards the mammal organism, is also not suitable for prophylaxis or therapy of HIV-virus infections {H. Mitsuya et al. "Suramin Protection of T-Cells in vitro against Infectivity and Cytopathic Effect of HTLV-III", Science 226 (1984), pages 172–174}.

Further development has led to reverse transcriptase inhibitors which are less toxic towards the mammal organism. These include substances such as dextran sulfate and pentosan polysulfate, which have proven to display a HIV-1-inhibiting effect in vivo, as has been described in DE 36 01 136 and in EP 0 293 826.

In addition to a chemotherapeutic treatment of HIV infections there is basically the possibility of a gene therapy or immunotherapy. Gene therapy comprises the incorporation of parts of viral nucleic acids in human cells, especially in the target cells of the HIV virus, for example the CD4-positive cells of the immune system. Then, the viral messenger RNA (m-RNA) can be neutralized by the formation of an "antisense" RNA, i.e. an RNA complementary to m-RNA, and hence the virus proliferation can be terminated. In some other form, oligonucleotides or structures chemical related thereto that are complementary to m-RNA can be employed. In immunotherapy, antigens are administered after the infection which are expected to support the immune response to HIV.

Meanwhile, the World Health Organization (WHO) estimates a number of at least 13 million of HIV-infected people worldwide; no country has been left free from infections with HIV-1 or HIV-2 or both viruses at the same time. It is urgently necessary to develop a vaccine for protection from HIV infections in order to prevent the epidemic from farther spreading. Here, and also in immunotherapy, the main problem is the high variability of the HIV viruses: a prophylactic inoculation should and must include all of the possible virus variants. Epidemiologic investigations in combination with the genetic characterization of the viruses produced the result that several subtypes do already exist in both virus families {Myers et al., Human Retroviruses and AIDS, Los Alamos, 1991; Dietrich et al., Nature 342, 948–950, 1989}, which subtypes are significantly distinguished from one another with respect to their hereditary information to a degree such that one single vaccine will not be capable to be active against all variants. Moreover, these subtypes are also subject to different geographic distributions.

The present invention provides three new HIV 1 virus isolates HIV-$1_{D757}$, HIV-$1_{D747}$, HIV-$1_{D760}$, which, surprisingly, form a further independent subtype of the HIV-1 family and have been recovered from three Indian patients who, at the time of virus isolation, did not show any typical AIDS symptoms. Furthermore, the invention also includes virus isolates of the HIV-1 type which are up to 30%, and preferably up to 5%, divergent from HIV-$1_{D757}$, HIV-$1_{D747}$, and HIV-$1_{D760}$.

The virus isolates, in accordance with the regulations according to the Budapest Treaty, have been deposited with the European Collection of Animal Cell Cultures (ECACC), Porton Down, Salisbury, Wiltshire, United Kingdom, on Aug. 27, 1992, under the following Accession Numbers:

HIV-$1_{D747}$—ECACC V92082718
HIV-$1_{D757}$—ECACC V92082719
HIV-$1_{D760}$—ECACC V92082720

The virus isolates proliferate on fresh mononuclear cells of peripheral blood, i.e. lymphocytes and macrophages.

The invention further provides a vaccine having an activity spectrum against this specific HIV-1 subtype.

The vaccine contains, as the active ingredient, the peptides

1. MPNGTKSNS SEQ ID NO: 7, MPNGTKGNS SEQ ID NO: 8, MPNGTKSNL SEQ ID NO: 9,
2. RNEKDLLALDSWKN SEQ ID NO: 10, combinations comprising said peptides or longer or shorter subpeptides thereof being up to 7 amino acids in length.

Said peptides are derived from the env region of the strains according to the invention (cf. FIG. 1). The nucleotide sequences of these viruses in the env gene over a range of 1.8 kb are only to 79.4–81.6% homologous with viruses of the North American/European subtype and to 78.9–81.2% homologous with prototype viruses of the Central African subtype. The homology on the amino acid level is 72.1–75.9% and 71.2–74.2%, respectively (cf. Table). Thus, these viruses genetically are to be classified between these two subtypes and form some further independent subtype which is also distinguished from the subtypes found in Rwanda/Uganda and in Northern Thailand by genetic equidistance.

Upon comparison of the amino acid sequences of the env proteins of HIV-$1_{D757}$, HIV-$1_{D747}$, HIV-$1_{D760}$ with the consensus sequences as derived for all of the HIV env sequences already published, there result for the env region two short ranges, in which the three Indian sequences are different from all of the other HIV-1 sequences in 7 of 9 and in 7 of 14 amino acids, respectively (FIG. 1). Peptides from these regions are preferably suitable for a vaccine having a specific spectrum of activity against the Indian subtype, and particularly so, if the vaccine consists of a combination of these peptides.

The peptides according to the invention are synthetically produced and, if advantageous, are chemically modified. These peptides or longer as well as shorter subpeptides, down to 7 amino acids in length, thereof are also a constituent of this invention, and so are their modified forms.

Furthermore, the invention also relates to a vaccine which contains, as the active ingredient, peptides from variable regions of other genes of HIV-1$_{D757}$, HIV-1$_{D747}$, HIV-1$_{D760}$, if the deviation from the corresponding sequence of HIV-1 viruses of other subtypes is more than 30%.

In the vaccine, there may further be used antigens from the viruses according to the invention or peptide combinations or combinations of peptides and antigens. More specifically, the use of such antigens or peptides is preferred which, within the loop of the coat glycoprotein (amino acids 423–450, relative to HIV-1$_{Lai}$), is responsible for binding to the CD4-receptor, contain a glycosylation site (NXT/S) immediately in front of cysteine 450 (HIV-1$_{Lai}$). This glycosylation site is typical for the Indian viruses HIV-1$_{D757}$, HIV-1$_{D747}$ und HIV-1$_{D760}$. This glycosylation site has not been encountered among 29 HIV-1 envgenes that have been sequenced worldwide.

One preferred embodiment is a vaccine which is employed for prophylaxis prior to infections. Another preferred embodiment consists of that the vaccine is used as an immunotherapeutic to be employed after the infection and also covers the spectrum of variants of this subtype. The vaccine is administered either for injection with adjuvant or as an oral, genital or rectal form of application, e.g. via nanoparticles.

Furtheron, the subject matter of the invention comprises a process for producing a vaccine against HIV-1 virus infections from the viruses HIV-1$_{D757}$, HIV-1$_{D747}$ and HIV-1$_{D760}$ as well as the use of these viruses for the production of a vaccine.

In still one further embodiment, the viruses HIV-1$_{D757}$, HIV-1$_{D747}$ and HIV-1$_{D760}$ are transferred into a suitable host animal and allowed to proliferate therein. Then, the antibodies formed, after appropriate work-up as also known in the art for other vaccines, are used as a passive vaccine against HIV virus infections. As the host animals, more particularly, there may be used, suitable types of monkeys, but also animals that can be immunized without developing HIV symptoms (e.g. rabbits) {Filice et al., Nature 335 (1988), 366–368}.

Human monoclonal antibodies against HIV-1$_{D757}$, HIV-1$_{D747}$ and HIV-1$_{D760}$ are also suitable for producing a vaccine for a protection against HIV-1 virus infections of this subtype.

In a further embodiment, in a suitable vector, DNA from which a RNA complementary to the viral m-RNA can be fully or partially transcribed, is transfected into human cells of the immune system and, hence, is conveyed into man. Thus, the viral m-RNA is competitively excluded from the further augmentation cycle. Likewise, synthetic oligonucleotides can be used for neutralizing the viral m-RNA.

In addition to the applications for therapy and vaccine production, HIV-1$_{D757}$, HIV-1$_{D747}$ and HIV-1$_{D760}$ can also be used for differential diagnostics in order to distinguish infections with this subtype from other subtypes. For differential diagnostics, selected regions of the DNA of HIV-1$_{D757}$, HIV-1$_{D747}$ and HIV-1$_{D760}$ are utilized which either do not occur at all in the prototype HIV-1$_{Lai}$ or are significantly different therefrom (by more than 30%). From these regions, peptides or nucleic acids for diagnostics are prepared according to conventional methods (labelling with radioactive isotopes, immunofluorescence test, ELISA etc.).

Therefore, it is also a constituent of this invention to use HIV-1$_{D757}$, HIV-1$_{D747}$ and HIV-1$_{D760}$, or antigens, peptides or nucleic acids thereof, for the differential diagnostics for differentiating between infections with the subtype, characterized by HIV-1$_{D757}$, HIV-1$_{D747}$ or HIV-1$_{D760}$, and infections with other HIV-1 subtypes as defined by the prototypes HIV-1$_{Lai}$ (U.S.A./Europe) HIV-1$_{Mal}$ (Central Africa), HIV-1$_{U455}$ (Uganda/Rwanda) and Northern Thailand.

It is also possible to employ peptide residues or PCR tests based on HIV-1$_{D757}$, HIV-1$_{D747}$ or HIV-1$_{D760}$, by means of which distinction can be made between viruses of this subtypes from other HIV-viruses.

Hereinbelow, the Figures and the Table are described:

The Table shows the nucleotide and amino acid sequence homology between HIV-1$_{D757}$, HIV-1$_{D747}$ or HIV-1$_{D760}$ and other HIV-1 virus subtypes in percent. The sequences were compared by using Mikrogenie™ sequencing software by the company Beckman.

FIG. 1 shows the amino acid sequences in single character notation of the three Indian env clones in comparison to the corresponding sections of other subtypes. Highlighted are the two peptides 1 and 2, in which the Indian subtype is mainly different from the other sequences, and the additional glycolisation site (underlined) in immediate vicinity to the CD4 binding domain.

(-) denotes identical amino acids;

(.) denotes missing aminoacids.

FIG. 2 shows the relation of the sequences HIV-1$_{D757}$, HIV-1$_{D747}$ or HIV-1$_{D760}$ to the remaining viruses in the phylogenetic tree of the viruses. This tree was established with the use of PAUP {Smith, T. F. et al., Nature 333, 573–575 (1988)} and the Version 3.21 of the PHYLIP bootstrappin algorithm.

TABLE

Homology of Indian HIV-1 isolates and American/European or prototypical African HIV-1 sequences (1.8 kb PCR-fragment, corresponding to positions 6129–7976 of HIV-1$_{Lai}$)

| HIV-1 | Lai | SF2 | Eli | Mal | SIVepz |
| --- | --- | --- | --- | --- | --- |
| D757 | 79.7 (75.7) | 81.6 (75.9) | 81.2 (74.2) | 80.6 (73.7) | 66.1 (61.2) |
| D747 | 79.4 (73.5) | 80.9 (75.6) | 80.7 (72.8) | 78.9 (73.2) | 65.8 (63.2) |
| D760 | 80.7 (72.1) | 81.4 (73.6) | 80.9 (71.2) | 80.2 (71.7) | 66.1 (61.0) |
| Lai |  | 90.0 (84.1) | 83.7 (76.2) | 82.8 (74.3) | 65.0 (60.1) |
| SF2 |  |  | 83.8 (75.6) | 82.8 (74.6) | 64.3 (62.0) |
| Eli |  |  |  | 85.2 (76.9) | 65.7 (61.9) |
| Mal |  |  |  |  | 66.4 (63.2) |

FIG. 1

```
HIV-1_Bru    -------------------S-K--DLGNATN-NSSN.TNSSSGEMMMEKG--------IS-
HIV-1_SF2    -----------------------DLGKATN-NSSN.WKEEI......KG--------I--
HIV-1_D757   SLWDQSLKPCVKLTPLCVTLNCTNA...NVTYDN..........GNYTEEIKNCSFNTTT
HIV-1_D747   ---------------------H----TYS-S--NS..........T.-N-----------
HIV-1_D760   ---------------------E-G-VNAT-I-NNGE...NNPTNIT--R------P--A--
HIV-1_Eli    ------------------SD-...ELRNNGTMGNNVTTEEK....GM------V--
HIV-1_Mal    -----------------------VNGTA-NGT-AGSNRTNAELKMEIG-V------I-P
SIVcpz       --------------------Q-SK-NFSQA.......KNLTNQTSSPPL-M------V--

HIV-1_Bru    SI-GKV--EY-F-----II-I-NDTT-......T-TS----V----------E-------
HIV-1_SF2    SI--KI--EN---RN-----I-NASTTTNYTN----H--R-V----------E-------
HIV-1_D757   ELRDQKQKVAALFYKLDVVPLDGNDNSS....YRLINCNTSAITQACPKVSFDPIPIHYC
HIV-1_D747   ----K----Q-----------NTT----...----------------------
HIV-1_D760   -I--RQ---Y----R--I----N-N--T....-----------------T---------
HIV-1_Eli    V-K-K--Q-Y----R--I--NDSSTNS.TN--------------------E-------
HIV-1_Mal    VGS-KR-E.Y-T--N--L-QI-D...-DN.SS----------V--------T---------
SIVcpz       ----K-KQ-YS---VE---N-GNEN-T......-I-----T--------T--E-------

HIV-1_Bru    ----F-----------------T----VQ-----R--------------E-VV---A-FT
HIV-1_SF2    T----F------------K---T----VQ-----R-I-------------E-VV---D-FT
HIV-1_D757   APAGYAILKCNNKTFNGTGPCHNVSTRTCTHGIKPVVSTQLLLNGSLAEGEIIIRSENLA
HIV-1_D747   -G------------------I--VQ---------------------------T
HIV-1_D760   --------------------VQ-----S------------------------T
HIV-1_Eli    ----F-----RD-K-------T----VQ-----R---------------E-V-------T
HIV-1_Mal    ----F------D-K----EI-K----VQ--------------------E--M------T
SIVcpz       ----F------D-D-S-K-K-T----VH---------T----I-------N-TV-V--KS HIV-1_Bru    D-A-----Q-----E-N---------------QR---RA-VTI-K-..NM--------RA-
HIV-1_SF2    --A-----Q--E--A-N------------Y-..---RA-HT--R------K------RAQ
HIV-1_D757   NNVKTIIVHLNQSVRIVCTRPNNNTRKSIRI..GPGQTFYATGDIIGDIRQAHCNISEGK
HIV-1_D747   ---------------E--Y---------GV--..---Q--------------------KH-
HIV-1_D760   D-------------EV---------------..---Q---------------------D-
HIV-1_Eli    --A-N--A---E--K-T-A--YQ---QRTP-...-L--SL-T-R.SRSI-G-------RAQ
HIV-1_Mal    D-T-N---Q--ET-T-N----G---RG-HF.....---AL-T--.-V----R-Y-T-N-TE
SIVcpz       K-TDVW--Q-VEA-SLN-H--G----GEVQ-..---M---NIENVV--T-S-Y-K-NGTT HIV-1_Bru    --A--KQIAS--R-Q-G-N--..-I-KQ----DP--V------G-------STQ-----WF
HIV-1_SF2    --N--EQIV---R-Q-G-N--..-V-NQ----DP--VM-------------TQLF.....
HIV-1_D757   WNETLQRVGKKLAEYFPN.KT.IKFASSSGGGLEITTHSFNCRGEFFYCNTSNLFNSTY.
HIV-1_D747   ---------------H----.--.-R--------D--------------------D---G--.
HIV-1_D760   ---------------H----.--.----A----D-----Y-------------G---G--.
HIV-1_Eli    -SK---Q-AR--GTLL.-KTI.---KP----DP---------G---------G-----WN
HIV-1_Mal    -DK---Q-AV--GSLL.-KTK.-I-N-----DP-------------------K-----WQ
```

-continued

FIG. 1

```
SIVcpz       --R-VEE-K-A--TSSNRTAAN-TLNRA---DP-V-H-M---G---------QI-.....
HIV-1_Bru    NSTWSTEGSNNTEGSD---LP-----F--------K-------S-Q-R-S--------T-
HIV-1_SF2    NNTWRLNHTEGTKG-D--ILP-------------K-------G-Q-S-S--------T-
HIV-1_D757   .....MPNGTKGNSNSTITIQCRIKQIINMWQEVGRAMYAPPIEGNITCESNITGLLLVR
HIV-1_D747   .....------S--S------P--------------------A-----K-----I----
HIV-1_D760   .....------S-L------P------V-L------------FAR----K---------
HIV-1_Eli    ISAWNNITESNNST-TN--L---------K-.VAGRK-I------R--L-S--------T-
HIV-1_Mal    NNG.ARLSNSTESTG-.--LP-----------KT-K-------A-V-N-L------I-T-
SIVcpz       .........-DNIT-GI-ILP---R--VSS-MR---GI-----R-----N--------TS
HIV-1_Bru    ---NN.--G.S-I---------D-------------K-E-------K------....Q---
HIV-1_SF2    ----NVT-D.T-V---------D------------IK-E---I---K-------....Q---
HIV-1_D757   DGGTESNNT..ETFRPGGG-MRNNWRSELYKYKVVEIKPLGVAPTTAKRRVV....EREK
HIV-1_D747   ---IEL-D-KT--------E-D-------------------------...----
HIV-1_D760   ---EDT-D..T-I-S-------D----------------------...----
HIV-1_Eli    ---..I--STN-----------D-------------Q-E-------R------...----
HIV-1_Mal    ---NS-D-SDN--L---------D--I----------R-E-------K------...----
SIVcpz       -TPVTN-SGNL.----T---N-KDI-----------R-E--S----K-R-HT-ARQKD-Q-
HIV-1_Bru    -----.---L--------------R--------------------N-------------
HIV-1_SF2    -----V--M--------------V-L------------------N-------------
HIV-1_D757   RAVGI.GAVFLGFLGAAGSTMGAASMTLTVQARQLLSGIVQQQSNLLRAIEAQQHLLQLT
HIV-1_D747   -----.----------------V----------------------
HIV-1_D760   ----L.----------------I----------------------
HIV-1_Eli    --I-L.--M-------------R-V---------M-------N----------------
HIV-1_Mal    --I-L.--M-------------L-------------N----------------
SIVcpz       --AFGL--L---------------AV------------------N---K-----------S
HIV-1_Bru    --------A-I--V-----------C--------A----A---.-K-LEQ-------
HIV-1_SF2    --------A----V----R--------C--------A----A---.-K-LED-------
HIV-1_D757   VWGIKQLQTRVLAIERYLKDQQLLGIWGRSGKLICTTNVPWNSSWS.NRSQTDIWDNMTW
HIV-1_D747   I-------A---------E--------C--------T--------.-------------
HIV-1_D760   ------------------M--C--------A--------.-------------
HIV-1_Eli    --------A-I--V-----------C---H-------------.---LNE--Q----
HIV-1_Mal    --------A----V----Q--R---M--C---H----F--------.---LD---N----
SIVcpz       I--V----A-L--V-----Q---I--L--C---AV-Y-T-------PGSN-TD---G-L--
HIV-1_Bru    -E---........................--N---SL-HS-I-E
HIV-1_SF2    ---E--........................-D---N---T---E
HIV-1_D757   MQWDR........................EISNYTDTIYRLLED
HIV-1_D747   -----........................------E--------
HIV-1_D760   -----........................------N--------
HIV-1_Eli    -E-E-........................--D---GL--S-I-E
```

```
FIG. 1
HIV-1_Mal    ---EK..........................................------GI--N-I-E
SIVcpz       Q---KLVSNYTGKIFGLLEEAQSQQEKNERDLLELDQWASLWNWFD-T---GK-FG---E
HIV-1_Bru    ------K--QE--E--K-AS-----N------------------V--R-V----------
HIV-1_SF2    ------K--QE--E--K-AS--------------------V--R-V----------
HIV-1_D757   SQNQQERNEKDLLALDSWKNLWNWFSITNWLWYIKIFIMIVGGLIGLKIIFAVLSIVNRV
HIV-1_D747   ----------------------------------------I--------R------C-----
HIV-1_D760   ------------------------------------------------R-------------
HIV-1_Eli    --T---K---E--E--K-AS--------Q-----------I------R-V-----L----
HIV-1_Mal    --I---K---E--E--K-AS--------SK-----R---IV-------R-------L----
SIVcpz       A-S---K--R---E--Q-AS-----D--K---------L-A---I---R--MT-F-V-R--
HIV-1_Bru    -----------
HIV-1_SF2    -----------
HIV-1_D757   RQGYSPLSFQT
HIV-1_D747   KA---------
HIV-1_D760   -----------
HIV-1_Eli    -----------
HIV-1_Mal    --------L--
SIVcpz       --------L--
```

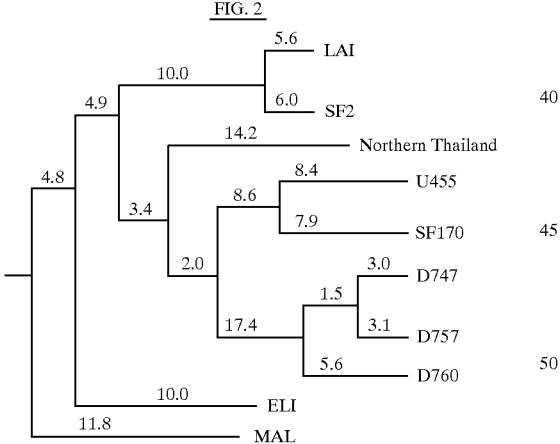

FIG. 2

We claim:

1. A polypeptide selected from the group consisting of SEQ ID NO: 2, SEQ ID NO: 4, and SEQ ID NO: 6.

2. A peptide selected from the group consisting of SEQ ID NO: 7, SEQ ID NO: 8, SEQ ID NO: 9, and SEQ ID NO: 10.

3. A process for producing antibodies comprising:
   a) injecting an animal with peptides selected from the group consisting of SEQ ID NO: 7, SEQ ID NO: 8, SEQ ID NO: 9, and SEQ ID NO: 10; and
   b) recovering the antibodies produced by the animal in response to the peptides.

4. A process for producing antibodies comprising:
   a) injecting an animal with polypeptides selected from the group consisting of SEQ ID NO: 2, SEQ ID NO: 4, and SEQ ID NO: 6; and
   b) recovering the antibodies produced by the animal in response to the polypeptides.

* * * * *

SEQUENCE LISTING (1) GENERAL INFORMATION:

(iii) NUMBER OF SEQUENCES: 10

(2) INFORMATION FOR SEQ ID NO:1:

```
    (i) SEQUENCE CHARACTERISTICS:
        (A) LENGTH: 1932 base pairs
        (B) TYPE: nucleic acid
        (C) STRANDEDNESS: unknown
        (D) TOPOLOGY: unknown (ii) MOLECULE TYPE: (genomic)

(vi) ORIGINAL SOURCE:
        (A) ORGANISM: HIV-1D757

(ix) FEATURE:
        (A) NAME/KEY: CDS
        (B) LOCATION: 2..1789

(xi) SEQUENCE DESCRIPTION: SEQ ID NO: 1:

C AGT TTA TGG GAT CAA AGC CTA AAG CCA TGT GTA AAG TTG ACC CCA          46
  Ser Leu Trp Asp Gln Ser Leu Lys Pro Cys Val Lys Leu Thr Pro
   1               5                  10                  15

CTC TGT GTC ACT TTA AAT TGT ACA AAT GCA AAT GTT ACC TAT GAT AAT        94
Leu Cys Val Thr Leu Asn Cys Thr Asn Ala Asn Val Thr Tyr Asp Asn
                 20                  25                  30

GGT AAC TAC ACT GAA GAA ATA AAA AAT TGC TCT TTC AAT ACA ACT ACA       142
Gly Asn Tyr Thr Glu Glu Ile Lys Asn Cys Ser Phe Asn Thr Thr Thr
             35                  40                  45

GAA CTA AGA GAT CAG AAA CAG AAA GTT GCT GCA CTT TTT TAT AAA CTT       190
Glu Leu Arg Asp Gln Lys Gln Lys Val Ala Ala Leu Phe Tyr Lys Leu
         50                  55                  60

GAT GTA GTA CCA CTT GAT GGT AAT GAT AAC TCT AGT TAT AGA TTA ATA       238
Asp Val Val Pro Leu Asp Gly Asn Asp Asn Ser Ser Tyr Arg Leu Ile
     65                  70                  75

AAT TGT AAT ACC TCA GCC ATA ACA CAA GCC TGT CCA AAG GTC TCT TTT       286
Asn Cys Asn Thr Ser Ala Ile Thr Gln Ala Cys Pro Lys Val Ser Phe
 80                  85                  90                  95

GAC CCA ATC CCT ATA CAT TAT TGT GCT CCA GCT GGT TAT GCG ATT CTA       334
Asp Pro Ile Pro Ile His Tyr Cys Ala Pro Ala Gly Tyr Ala Ile Leu
                100                 105                 110

AAG TGT AAT AAT AAG ACA TTC AAT GGG ACA GGA CCA TGC CAT AAT GTC       382
Lys Cys Asn Asn Lys Thr Phe Asn Gly Thr Gly Pro Cys His Asn Val
            115                 120                 125

AGC ACA CGT ACA TGT ACA CAT GGA ATT AAG CCA GTA GTA TCA ACT CAA       430
Ser Thr Arg Thr Cys Thr His Gly Ile Lys Pro Val Val Ser Thr Gln
        130                 135                 140

CTA CTG TTA AAT GGT AGC CTA GCA GAA GGA GAG ATA ATA ATT AGA TCT       478
Leu Leu Leu Asn Gly Ser Leu Ala Glu Gly Glu Ile Ile Ile Arg Ser
    145                 150                 155

GAA AAT CTG GCA AAC AAT GTC AAA ACA ATA ATA GTA CAT CTT AAT CAA       526
Glu Asn Leu Ala Asn Asn Val Lys Thr Ile Ile Val His Leu Asn Gln
160                 165                 170                 175

TCT GTA AGA ATT GTG TGT ACA AGA CCC AAC AAT AAT ACA AGA AAA AGT       574
Ser Val Arg Ile Val Cys Thr Arg Pro Asn Asn Asn Thr Arg Lys Ser
                180                 185                 190

ATA AGG ATA GGA CCA GGA CAA ACA TTC TAT GCA ACA GGA GAC ATA ATA       622
Ile Arg Ile Gly Pro Gly Gln Thr Phe Tyr Ala Thr Gly Asp Ile Ile
            195                 200                 205

GGA GAC ATA AGA CAA GCA CAT TGT AAC ATT AGT GAA GGT AAA TGG AAT       670
Gly Asp Ile Arg Gln Ala His Cys Asn Ile Ser Glu Gly Lys Trp Asn
        210                 215                 220

GAA ACT TTA CAA AGG GTA GGT AAA AAA TTA GCA GAA TAC TTC CCT AAT       718
Glu Thr Leu Gln Arg Val Gly Lys Lys Leu Ala Glu Tyr Phe Pro Asn
    225                 230                 235

AAA ACA ATA AAA TTT GCA TCA TCC TCA GGA GGG GGC CTA GAA ATT ACA       766
Lys Thr Ile Lys Phe Ala Ser Ser Ser Gly Gly Gly Leu Glu Ile Thr
240                 245                 250                 255
```

```
ACA CAT AGC TTT AAT TGT AGA GGA GAA TTT TTC TAT TGC AAT ACA TCA          814
Thr His Ser Phe Asn Cys Arg Gly Glu Phe Phe Tyr Cys Asn Thr Ser
            260                 265                 270

AAC CTG TTT AAT AGT ACA TAC ATG CCT AAT GGT ACA AAA GGT AAT TCA          862
Asn Leu Phe Asn Ser Thr Tyr Met Pro Asn Gly Thr Lys Gly Asn Ser
            275                 280                 285

AAC TCA ACC ATC ACA ATC CAA TGC AGA ATA AAA CAA ATT ATA AAC ATG          910
Asn Ser Thr Ile Thr Ile Gln Cys Arg Ile Lys Gln Ile Ile Asn Met
            290                 295                 300

TGG CAG GAG GTA GGA CGA GCA ATG TAT GCC CCT CCC ATT GAA GGA AAC          958
Trp Gln Glu Val Gly Arg Ala Met Tyr Ala Pro Pro Ile Glu Gly Asn
            305                 310                 315

ATA ACG TGT GAA TCC AAT ATC ACA GGA CTA CTA TTG GTA CGT GAT GGA         1006
Ile Thr Cys Glu Ser Asn Ile Thr Gly Leu Leu Leu Val Arg Asp Gly
320                 325                 330                 335

GGA ACA GAG TCA AAT AAT ACA GAG ACA TTC AGA CCT GGA GGA GGA GAT         1054
Gly Thr Glu Ser Asn Asn Thr Glu Thr Phe Arg Pro Gly Gly Gly Asp
            340                 345                 350

ATG AGG AAC AAT TGG AGA AGT GAA TTA TAT AAA TAT AAA GTG GTA GAA         1102
Met Arg Asn Asn Trp Arg Ser Glu Leu Tyr Lys Tyr Lys Val Val Glu
            355                 360                 365

ATT AAG CCA TTG GGA GTA GCG CCC ACT ACT GCA AAA AGG AGA GTG GTG         1150
Ile Lys Pro Leu Gly Val Ala Pro Thr Thr Ala Lys Arg Arg Val Val
            370                 375                 380

GAG AGA GAA AAA AGA GCA GTG GGA ATA GGA GCT GTG TTC CTT GGG TTC         1198
Glu Arg Glu Lys Arg Ala Val Gly Ile Gly Ala Val Phe Leu Gly Phe
385                 390                 395

TTG GGA GCA GCA GGA AGC ACT ATG GGC GCG GCA TCA ATG ACG CTG ACG         1246
Leu Gly Ala Ala Gly Ser Thr Met Gly Ala Ala Ser Met Thr Leu Thr
400                 405                 410                 415

GTA CAG GCC AGA CAA TTG TTG TCT GGT ATA GTG CAA CAG CAA AGC AAT         1294
Val Gln Ala Arg Gln Leu Leu Ser Gly Ile Val Gln Gln Gln Ser Asn
            420                 425                 430

TTG CTG AGG GCT ATA GAG GCG CAA CAG CAT CTG TTG CAA CTC ACG GTC         1342
Leu Leu Arg Ala Ile Glu Ala Gln Gln His Leu Leu Gln Leu Thr Val
            435                 440                 445

TGG GGC ATT AAG CAG CTC CAG ACA AGA GTC CTG GCT ATA GAA AGA TAC         1390
Trp Gly Ile Lys Gln Leu Gln Thr Arg Val Leu Ala Ile Glu Arg Tyr
            450                 455                 460

CTA AAG GAT CAA CAG CTC CTA GGG ATT TGG GGC CGC TCT GGA AAA CTC         1438
Leu Lys Asp Gln Gln Leu Leu Gly Ile Trp Gly Arg Ser Gly Lys Leu
465                 470                 475

ATC TGC ACC ACT AAT GTA CCT TGG AAC TCC AGC TGG AGT AAC AGA TCT         1486
Ile Cys Thr Thr Asn Val Pro Trp Asn Ser Ser Trp Ser Asn Arg Ser
480                 485                 490                 495

CAA ACA GAT ATT TGG GAT AAC ATG ACC TGG ATG CAG TGG GAT AGA GAA         1534
Gln Thr Asp Ile Trp Asp Asn Met Thr Trp Met Gln Trp Asp Arg Glu
            500                 505                 510

ATT AGT AAT TAC ACA GAC ACA ATA TAC AGG TTG CTT GAA GAC TCG CAA         1582
Ile Ser Asn Tyr Thr Asp Thr Ile Tyr Arg Leu Leu Glu Asp Ser Gln
            515                 520                 525

AAC CAG CAG GAA AGA AAT GAA AAA GAT TTA TTA GCA TTG GAC AGT TGG         1630
Asn Gln Gln Glu Arg Asn Glu Lys Asp Leu Leu Ala Leu Asp Ser Trp
            530                 535                 540

AAA AAT CTG TGG AAT TGG TTT AGC ATA ACA AAT TGG CTG TGG TAT ATA         1678
Lys Asn Leu Trp Asn Trp Phe Ser Ile Thr Asn Trp Leu Trp Tyr Ile
            545                 550                 555

AAA ATA TTC ATA ATG ATA GTA GGA GGC TTG ATA GGT TTA AAA ATA ATT         1726
Lys Ile Phe Ile Met Ile Val Gly Gly Leu Ile Gly Leu Lys Ile Ile
560                 565                 570                 575
```

```
TTT GCT GTG CTC TCT ATA GTG AAT AGA GTT AGG CAG GGA TAC TCA CCT        1774
Phe Ala Val Leu Ser Ile Val Asn Arg Val Arg Gln Gly Tyr Ser Pro
                580                 585                 590

TTA TCG TTT CAG ACC CTTACCCCGA ACCCAGGGGG ACCCGACAGG CTCGAAAGAA        1829
Leu Ser Phe Gln Thr
            595

TCGAAGGAGG AGGTGGAGAG CAAGACAAAG ACAGATCCAT TCGCTTAGTG AACGGATTCT      1889

TAGCACTTGC CTGGGACGAC TGCGGAGCCT GTGCCTCTTC AGC                        1932
```

(2) INFORMATION FOR SEQ ID NO: 2:

(i) SEQUENCE CHARACTERISTICS:
        (A) LENGTH: 596 amino acids
        (B) TYPE: amino acid
        (D) TOPOLOGY: linear (ii) MOLECULE TYPE: protein (xi) SEQUENCE DESCRIPTION: SEQ ID NO: 2:

```
Ser Leu Trp Asp Gln Ser Leu Lys Pro Cys Val Lys Leu Thr Pro Leu
 1               5                  10                  15

Cys Val Thr Leu Asn Cys Thr Asn Ala Asn Val Thr Tyr Asp Asn Gly
                20                  25                  30

Asn Tyr Thr Glu Glu Ile Lys Asn Cys Ser Phe Asn Thr Thr Thr Glu
                35                  40                  45

Leu Arg Asp Gln Lys Gln Lys Val Ala Ala Leu Phe Tyr Lys Leu Asp
     50                  55                  60

Val Val Pro Leu Asp Gly Asn Asp Ser Ser Tyr Arg Leu Ile Asn
 65                  70                  75                  80

Cys Asn Thr Ser Ala Ile Thr Gln Ala Cys Pro Lys Val Ser Phe Asp
                85                  90                  95

Pro Ile Pro Ile His Tyr Cys Ala Pro Ala Gly Tyr Ala Ile Leu Lys
                100                 105                 110

Cys Asn Asn Lys Thr Phe Asn Gly Thr Gly Pro Cys His Asn Val Ser
            115                 120                 125

Thr Arg Thr Cys Thr His Gly Ile Lys Pro Val Val Ser Thr Gln Leu
    130                 135                 140

Leu Leu Asn Gly Ser Leu Ala Glu Gly Glu Ile Ile Arg Ser Glu
145                 150                 155                 160

Asn Leu Ala Asn Asn Val Lys Thr Ile Ile Val His Leu Asn Gln Ser
                165                 170                 175

Val Arg Ile Val Cys Thr Arg Pro Asn Asn Asn Thr Arg Lys Ser Ile
                180                 185                 190

Arg Ile Gly Pro Gly Gln Thr Phe Tyr Ala Thr Gly Asp Ile Ile Gly
            195                 200                 205

Asp Ile Arg Gln Ala His Cys Asn Ile Ser Glu Gly Lys Trp Asn Glu
    210                 215                 220

Thr Leu Gln Arg Val Gly Lys Lys Leu Ala Glu Tyr Phe Pro Asn Lys
225                 230                 235                 240

Thr Ile Lys Phe Ala Ser Ser Ser Gly Gly Gly Leu Glu Ile Thr Thr
                245                 250                 255

His Ser Phe Asn Cys Arg Gly Glu Phe Phe Tyr Cys Asn Thr Ser Asn
                260                 265                 270

Leu Phe Asn Ser Thr Tyr Met Pro Asn Gly Thr Lys Gly Asn Ser Asn
            275                 280                 285

Ser Thr Ile Thr Ile Gln Cys Arg Ile Lys Gln Ile Ile Asn Met Trp
```

```
              290                 295                 300
Gln Glu Val Gly Arg Ala Met Tyr Ala Pro Pro Ile Glu Gly Asn Ile
305                 310                 315                 320

Thr Cys Glu Ser Asn Ile Thr Gly Leu Leu Val Arg Asp Gly Gly
                325                 330                 335

Thr Glu Ser Asn Asn Thr Glu Thr Phe Arg Pro Gly Gly Asp Met
                340                 345                 350

Arg Asn Asn Trp Arg Ser Glu Leu Tyr Lys Tyr Lys Val Val Glu Ile
                355                 360                 365

Lys Pro Leu Gly Val Ala Pro Thr Thr Ala Lys Arg Arg Val Val Glu
370                 375                 380

Arg Glu Lys Arg Ala Val Gly Ile Gly Ala Val Phe Leu Gly Phe Leu
385                 390                 395                 400

Gly Ala Ala Gly Ser Thr Met Gly Ala Ala Ser Met Thr Leu Thr Val
                405                 410                 415

Gln Ala Arg Gln Leu Leu Ser Gly Ile Val Gln Gln Ser Asn Leu
                420                 425                 430

Leu Arg Ala Ile Glu Ala Gln Gln His Leu Leu Gln Leu Thr Val Trp
                435                 440                 445

Gly Ile Lys Gln Leu Gln Thr Arg Val Leu Ala Ile Glu Arg Tyr Leu
450                 455                 460

Lys Asp Gln Gln Leu Leu Gly Ile Trp Gly Arg Ser Gly Lys Leu Ile
465                 470                 475                 480

Cys Thr Thr Asn Val Pro Trp Asn Ser Ser Trp Ser Asn Arg Ser Gln
                485                 490                 495

Thr Asp Ile Trp Asp Asn Met Thr Trp Met Gln Trp Asp Arg Glu Ile
                500                 505                 510

Ser Asn Tyr Thr Asp Thr Ile Tyr Arg Leu Leu Glu Asp Ser Gln Asn
                515                 520                 525

Gln Gln Glu Arg Asn Glu Lys Asp Leu Leu Ala Leu Asp Ser Trp Lys
                530                 535                 540

Asn Leu Trp Asn Trp Phe Ser Ile Thr Asn Trp Leu Trp Tyr Ile Lys
545                 550                 555                 560

Ile Phe Ile Met Ile Val Gly Gly Leu Ile Gly Leu Lys Ile Ile Phe
                565                 570                 575

Ala Val Leu Ser Ile Val Asn Arg Val Arg Gln Gly Tyr Ser Pro Leu
                580                 585                 590

Ser Phe Gln Thr
                595

(2) INFORMATION FOR SEQ ID NO: 3:

(i) SEQUENCE CHARACTERISTICS:
        (A) LENGTH: 1944 base pairs
        (B) TYPE: nucleic acid
        (C) STRANDEDNESS: unknown
        (D) TOPOLOGY: unknown (ii) MOLECULE TYPE: DNA (genomic)

(vi) ORIGINAL SOURCE:
        (A) ORGANISM: HIV-1D747

(ix) FEATURE:
        (A) NAME/KEY: CDS
        (B) LOCATION: 131..1930

(xi) SEQUENCE DESCRIPTION: SEQ ID NO: 3:

TAATGTCTGG GCAACACATG CCTGTGTACC CACAGACCCC AACCCACAAG AGATGGTTTT      60
```

```
GGGAAATGTA ACAGAAAATT TTAACATGTG AGAAATGAC ATGGTGAATC AGATGCATGA        120

GGATGTAATC AGT TTA TGG GAT CAA AGC CTA AAG CCA TGT GTA AAG TTG         169
           Ser Leu Trp Asp Gln Ser Leu Lys Pro Cys Val Lys Leu
            1               5                  10

ACC CCA CTC TGT GTC ACT TTA CAT TGT ACA AAT GCT ACC TAT AGT AAT        217
Thr Pro Leu Cys Val Thr Leu His Cys Thr Asn Ala Thr Tyr Ser Asn
    15              20                  25

AGT ACC TAC AAT AGT ACC TAC AAT GAA GAA ATA AAA AAT TGC TCT TTC        265
Ser Thr Tyr Asn Ser Thr Tyr Asn Glu Glu Ile Lys Asn Cys Ser Phe
30              35                  40                  45

AAT ACA ACT ACG GAA CTA AGA GAT AAG AAA CAG AAA GTA CAA GCA CTT        313
Asn Thr Thr Thr Glu Leu Arg Asp Lys Lys Gln Lys Val Gln Ala Leu
                50                  55                  60

TTT TAT AAA CTT GAT GTA GTA CCA CTT AAT ACT ACT GAT AAC TCT AGT        361
Phe Tyr Lys Leu Asp Val Val Pro Leu Asn Thr Thr Asp Asn Ser Ser
            65                  70                  75

TAT AGA TTA ATA AAT TGT AAT ACC TCA GCC ATA ACA CAA GCC TGT CCA        409
Tyr Arg Leu Ile Asn Cys Asn Thr Ser Ala Ile Thr Gln Ala Cys Pro
            80                  85                  90

AAG GTC TCA TTT GAC CCA ATT CCT ATA CAT TAT TGT GCT GGA GCT GGT        457
Lys Val Ser Phe Asp Pro Ile Pro Ile His Tyr Cys Ala Gly Ala Gly
        95                 100                 105

TAT GCG ATT CTA AAG TGT AAT AAT AAG ACA TTC AAT GGG ACA GGA CCA        505
Tyr Ala Ile Leu Lys Cys Asn Asn Lys Thr Phe Asn Gly Thr Gly Pro
110             115                 120                 125

TGC CAT AAT ATC AGC ACA GTA CAA TGT ACA CAT GGA ATT AAG CCA GTA        553
Cys His Asn Ile Ser Thr Val Gln Cys Thr His Gly Ile Lys Pro Val
                130                 135                 140

GTA TCA ACT CAA CTA CTG TTA AAT GGT AGC CTA GCA GAA GGA GAG ATA        601
Val Ser Thr Gln Leu Leu Leu Asn Gly Ser Leu Ala Glu Gly Glu Ile
            145                 150                 155

ATA ATT AGA TCT GAA AAT CTG ACA AAC AAT GTC AAA ACA ATA ATA GTA        649
Ile Ile Arg Ser Glu Asn Leu Thr Asn Asn Val Lys Thr Ile Ile Val
            160                 165                 170

CAT CTT AAT CAA TCT GTA GAA ATT GTG TAT ACA AGA CCC AAC AAT AAT        697
His Leu Asn Gln Ser Val Glu Ile Val Tyr Thr Arg Pro Asn Asn Asn
175                 180                 185

ACA AGG AAA GGT GTA AGG ATA GGA CCA GGA CAA ACA TTC TAT GCA ACA        745
Thr Arg Lys Gly Val Arg Ile Gly Pro Gly Gln Thr Phe Tyr Ala Thr
190                 195                 200                 205

GGA GAC ATA ATA GGA GAC ATA AGA CAA GCA CAT TGT AAC ATT AGT AAA        793
Gly Asp Ile Ile Gly Asp Ile Arg Gln Ala His Cys Asn Ile Ser Lys
                210                 215                 220

CAT AAA TGG AAT GAA ACT TTA CAA AGG GTA GGT AAA AAA TTA GCA GAA        841
His Lys Trp Asn Glu Thr Leu Gln Arg Val Gly Lys Lys Leu Ala Glu
            225                 230                 235

CAC TTC CCT AAT AAA ACA ATA AGA TTT GCA TCA TCC TCA GGA GGG GAC        889
His Phe Pro Asn Lys Thr Ile Arg Phe Ala Ser Ser Ser Gly Gly Asp
            240                 245                 250

CTA GAA ATT ACA ACA CAT AGC TTT AAT TGT AGA GGA GAA TTT TTC TAT        937
Leu Glu Ile Thr Thr His Ser Phe Asn Cys Arg Gly Glu Phe Phe Tyr
        255                 260                 265

TGC AAT ACA TCA GAC CTG TTT AAT GGT ACA TAC ATG CCT AAT GGT ACA        985
Cys Asn Thr Ser Asp Leu Phe Asn Gly Thr Tyr Met Pro Asn Gly Thr
270                 275                 280                 285

AAA AGT AAT TCA AGC TCA ACC ATC ACA ATT CCA TGC AGA ATA AAA CAA       1033
Lys Ser Asn Ser Ser Ser Thr Ile Thr Ile Pro Cys Arg Ile Lys Gln
                290                 295                 300

ATT ATA AAC ATG TGG CAG GAG GTA GGA CGA GCA ATG TAT GCC CCT CCC       1081
```

```
Ile Ile Asn Met Trp Gln Glu Val Gly Arg Ala Met Tyr Ala Pro Pro
            305                 310                 315

ATT GCA GGA AAC ATA ACG TGT AAA TCC AAT ATT ACA GGA ATA CTA TTG      1129
Ile Ala Gly Asn Ile Thr Cys Lys Ser Asn Ile Thr Gly Ile Leu Leu
            320                 325                 330

GTA CGT GAT GGA GGA ATA GAG CTA AAT GAT ACA AAG ACA GAG ACA TTC      1177
Val Arg Asp Gly Gly Ile Glu Leu Asn Asp Thr Lys Thr Glu Thr Phe
335                 340                 345

AGA CCG GGA GGA GGA GAA ATG AGG GAC AAT TGG AGA AGT GAA TTA TAT      1225
Arg Pro Gly Gly Gly Glu Met Arg Asp Asn Trp Arg Ser Glu Leu Tyr
350                 355                 360                 365

AAA TAT AAA GTG GTA GAA ATT AAG CCA TTG GGA GTA GCG CCC ACT ACT      1273
Lys Tyr Lys Val Val Glu Ile Lys Pro Leu Gly Val Ala Pro Thr Thr
            370                 375                 380

GCA AAA AGG AGA GTG GTG GAG AGA GAA AAA AGA GCA GTG GGA ATA GGA      1321
Ala Lys Arg Arg Val Val Glu Arg Glu Lys Arg Ala Val Gly Ile Gly
            385                 390                 395

GCT GTA TTC CTT GGG TTC TTG GGA GCA GCA GGA AGC ACT ATG GGC GCG      1369
Ala Val Phe Leu Gly Phe Leu Gly Ala Ala Gly Ser Thr Met Gly Ala
            400                 405                 410

GCG TCA ATG ACC GTG ACG GTA CAG GCC AGA CAA TTG TTG TCT GGT ATA      1417
Ala Ser Met Thr Val Thr Val Gln Ala Arg Gln Leu Leu Ser Gly Ile
            415                 420                 425

GTG CAA CAG CAA AGC AAT TTG CTG AGG GCT ATA GAG GCG CAA CAG CAT      1465
Val Gln Gln Gln Ser Asn Leu Leu Arg Ala Ile Glu Ala Gln Gln His
430                 435                 440                 445

CTG TTG CAA CTC ACG ATC TGG GGG ATT AAG CAG CTC CAG GCA AGA GTC      1513
Leu Leu Gln Leu Thr Ile Trp Gly Ile Lys Gln Leu Gln Ala Arg Val
            450                 455                 460

CTG GCT ATA GAA AGA TAC CTA AAG GAA CAA CAG CTC CTA GGG ATT TGG      1561
Leu Ala Ile Glu Arg Tyr Leu Lys Glu Gln Gln Leu Leu Gly Ile Trp
            465                 470                 475

GGC TGC TCT GGA AAA CTC ATC TGC ACC ACT ACT GTA CCT TGG AAC TCC      1609
Gly Cys Ser Gly Lys Leu Ile Cys Thr Thr Thr Val Pro Trp Asn Ser
            480                 485                 490

AGT TGG AGT AAC AGA TCT CAA ACA GAT ATT TGG GAT AAC ATG ACC TGG      1657
Ser Trp Ser Asn Arg Ser Gln Thr Asp Ile Trp Asp Asn Met Thr Trp
495                 500                 505

ATG CAG TGG GAT AGA GAA ATT AGT AAT TAC ACA GAA ACA ATA TAC AGG      1705
Met Gln Trp Asp Arg Glu Ile Ser Asn Tyr Thr Glu Thr Ile Tyr Arg
510                 515                 520                 525

TTG CTT GAA GAC TCG CAA AAC CAG CAG GAA AGA AAT GAA AAA GAT TTA      1753
Leu Leu Glu Asp Ser Gln Asn Gln Gln Glu Arg Asn Glu Lys Asp Leu
            530                 535                 540

TTA GCA TTG GAC AGT TGG AAA AAT CTG TGG AAT TGG TTT AGC ATA ACA      1801
Leu Ala Leu Asp Ser Trp Lys Asn Leu Trp Asn Trp Phe Ser Ile Thr
            545                 550                 555

AAT TGG CTA TGG TAT ATA AAA ATA TTC ATA ATA ATA GTA GGA GGC TTG      1849
Asn Trp Leu Trp Tyr Ile Lys Ile Phe Ile Ile Ile Val Gly Gly Leu
            560                 565                 570

ATA GGC TTG AGA ATA ATT TTT GCT GTG CTT TGT ATA GTA AAT AGA GTT      1897
Ile Gly Leu Arg Ile Ile Phe Ala Val Leu Cys Ile Val Asn Arg Val
            575                 580                 585

AAG GCA GGA TAC TCA CCT TTG TCG TTT CAG ACC CTTACCCCGA ACCC          1944
Lys Ala Gly Tyr Ser Pro Leu Ser Phe Gln Thr
590                 595                 600
```

(2) INFORMATION FOR SEQ ID NO: 4:

(i) SEQUENCE CHARACTERISTICS:
        (A) LENGTH: 600 amino acids (B) TYPE: amino acid
(D) TOPOLOGY: linear (ii) MOLECULE TYPE: protein (xi) SEQUENCE DESCRIPTION: SEQ ID NO: 4:

```
Ser Leu Trp Asp Gln Ser Leu Lys Pro Cys Val Lys Leu Thr Pro Leu
 1               5                  10                  15

Cys Val Thr Leu His Cys Thr Asn Ala Thr Tyr Ser Asn Ser Thr Tyr
                20                  25                  30

Asn Ser Thr Tyr Asn Glu Glu Ile Lys Asn Cys Ser Phe Asn Thr Thr
                35                  40                  45

Thr Glu Leu Arg Asp Lys Lys Gln Lys Val Gln Ala Leu Phe Tyr Lys
        50                  55                  60

Leu Asp Val Val Pro Leu Asn Thr Thr Asp Asn Ser Ser Tyr Arg Leu
 65                  70                  75                  80

Ile Asn Cys Asn Thr Ser Ala Ile Thr Gln Ala Cys Pro Lys Val Ser
                85                  90                  95

Phe Asp Pro Ile Pro Ile His Tyr Cys Ala Gly Ala Gly Tyr Ala Ile
                100                 105                 110

Leu Lys Cys Asn Asn Lys Thr Phe Asn Gly Thr Gly Pro Cys His Asn
        115                 120                 125

Ile Ser Thr Val Gln Cys Thr His Gly Ile Lys Pro Val Val Ser Thr
130                 135                 140

Gln Leu Leu Leu Asn Gly Ser Leu Ala Glu Glu Ile Ile Ile Arg
145                 150                 155                 160

Ser Glu Asn Leu Thr Asn Asn Val Lys Thr Ile Ile Val His Leu Asn
                165                 170                 175

Gln Ser Val Glu Ile Val Tyr Thr Arg Pro Asn Asn Asn Thr Arg Lys
                180                 185                 190

Gly Val Arg Ile Gly Pro Gly Gln Thr Phe Tyr Ala Thr Gly Asp Ile
        195                 200                 205

Ile Gly Asp Ile Arg Gln Ala His Cys Asn Ile Ser Lys His Lys Trp
210                 215                 220

Asn Glu Thr Leu Gln Arg Val Gly Lys Lys Leu Ala Glu His Phe Pro
225                 230                 235                 240

Asn Lys Thr Ile Arg Phe Ala Ser Ser Ser Gly Gly Asp Leu Glu Ile
                245                 250                 255

Thr Thr His Ser Phe Asn Cys Arg Gly Glu Phe Phe Tyr Cys Asn Thr
                260                 265                 270

Ser Asp Leu Phe Asn Gly Thr Tyr Met Pro Asn Gly Thr Lys Ser Asn
        275                 280                 285

Ser Ser Ser Thr Ile Thr Ile Pro Cys Arg Ile Lys Gln Ile Ile Asn
290                 295                 300

Met Trp Gln Glu Val Gly Arg Ala Met Tyr Ala Pro Pro Ile Ala Gly
305                 310                 315                 320

Asn Ile Thr Cys Lys Ser Asn Ile Thr Gly Ile Leu Leu Val Arg Asp
                325                 330                 335

Gly Gly Ile Glu Leu Asn Asp Thr Lys Thr Glu Thr Phe Arg Pro Gly
                340                 345                 350

Gly Gly Glu Met Arg Asp Asn Trp Arg Ser Glu Leu Tyr Lys Tyr Lys
        355                 360                 365

Val Val Glu Ile Lys Pro Leu Gly Val Ala Pro Thr Thr Ala Lys Arg
370                 375                 380

Arg Val Val Glu Arg Glu Lys Arg Ala Val Gly Ile Gly Ala Val Phe
```

```
385                 390                 395                 400
Leu Gly Phe Leu Gly Ala Ala Gly Ser Thr Met Gly Ala Ala Ser Met
                405                 410                 415

Thr Val Thr Val Gln Ala Arg Gln Leu Leu Ser Gly Ile Val Gln Gln
            420                 425                 430

Gln Ser Asn Leu Leu Arg Ala Ile Glu Ala Gln Gln His Leu Leu Gln
        435                 440                 445

Leu Thr Ile Trp Gly Ile Lys Gln Leu Gln Ala Arg Val Leu Ala Ile
    450                 455                 460

Glu Arg Tyr Leu Lys Glu Gln Gln Leu Leu Gly Ile Trp Gly Cys Ser
465                 470                 475                 480

Gly Lys Leu Ile Cys Thr Thr Thr Val Pro Trp Asn Ser Ser Trp Ser
                485                 490                 495

Asn Arg Ser Gln Thr Asp Ile Trp Asp Asn Met Thr Trp Met Gln Trp
            500                 505                 510

Asp Arg Glu Ile Ser Asn Tyr Thr Glu Thr Ile Tyr Arg Leu Leu Glu
        515                 520                 525

Asp Ser Gln Asn Gln Gln Glu Arg Asn Glu Lys Asp Leu Leu Ala Leu
    530                 535                 540

Asp Ser Trp Lys Asn Leu Trp Asn Trp Phe Ser Ile Thr Asn Trp Leu
545                 550                 555                 560

Trp Tyr Ile Lys Ile Phe Ile Ile Val Gly Leu Ile Gly Leu
                565                 570                 575   Arg

Arg Ile Ile Phe Ala Val Leu Cys Ile Val Asn Arg Val Lys Ala Gly
                580                 585                 590

Tyr Ser Pro Leu Ser Phe Gln Thr
                595                 600

(2) INFORMATION FOR SEQ ID NO: 5:

(i) SEQUENCE CHARACTERISTICS:
        (A) LENGTH: 1952 base pairs
        (B) TYPE: nucleic acid
        (C) STRANDEDNESS: unknown
        (D) TOPOLOGY: unknown (ii) MOLECULE TYPE: DNA (genomic)

(vi) ORIGINAL SOURCE:
        (A) ORGANISM: HIV-1D760

(ix) FEATURE:
        (A) NAME/KEY: CDS
        (B) LOCATION: 133..1950

(xi) SEQUENCE DESCRIPTION: SEQ ID NO: 5:

CATAATGTCT GGGCTACATA TGCCTGTGTA CCCACAGGCC CCGACCCACA AGAAATAGTT      60

TTGGAAAATG TAACAGGAAA TTTTAACATG TGGAAAAATG ACATGGTGGA TCAAATGCAT     120

GAGGATGTAA TC AGT TTA TGG GAT CAA AGC CTA AAG CCA TGT GTA AAG         168
              Ser Leu Trp Asp Gln Ser Leu Lys Pro Cys Val Lys
                1               5                  10

TTG ACC CCA CTC TGT GTC ACT TTA GAG TGT GGA AAT GTT AAT GCT ACC       216
Leu Thr Pro Leu Cys Val Thr Leu Glu Cys Gly Asn Val Asn Ala Thr
            15                  20                  25

AAT ATT ACC AAT AAT GGG GAA AAT AAT CCT ACC AAT ATT ACC AAT AAT       264
Asn Ile Thr Asn Asn Gly Glu Asn Asn Pro Thr Asn Ile Thr Asn Asn
        30                  35                  40

AGG GAA GAA ATA AAA AAT TGC CCT TTC AAT GCA ACC ACA GAA ATA AGA       312
Arg Glu Glu Ile Lys Asn Cys Pro Phe Asn Ala Thr Thr Glu Ile Arg
    45                  50                  55                  60
```

-continued

```
GAT AGG CAG CAG AAA GTG TAT GCA CTT TTT TAT AGA CTT GAT ATA GTA      360
Asp Arg Gln Gln Lys Val Tyr Ala Leu Phe Tyr Arg Leu Asp Ile Val
                65                  70                  75

CCA CTT GAT AAT AAT AAT AAT AGC ACC TAT AGA TTA ATA AAT TGT AAT      408
Pro Leu Asp Asn Asn Asn Asn Ser Thr Tyr Arg Leu Ile Asn Cys Asn
                    80                  85                  90

ACC TCA GCC ATA ACA CAA GCC TGT CCA AAG GTC ACT TTT GAT CCA ATT      456
Thr Ser Ala Ile Thr Gln Ala Cys Pro Lys Val Thr Phe Asp Pro Ile
            95                 100                 105

CCT ATA CAC TAT TGT GCT CCA GCT GGT TAT GCG ATT CTA AAG TGT AAT      504
Pro Ile His Tyr Cys Ala Pro Ala Gly Tyr Ala Ile Leu Lys Cys Asn
110                 115                 120

AAT AAG ACA TTC AAT GGG ACA GGA CCA TGC CAT AAT GTC AGC ACA GTA      552
Asn Lys Thr Phe Asn Gly Thr Gly Pro Cys His Asn Val Ser Thr Val
125                 130                 135                 140

CAA TGT ACA CAT GGA ATT AGC CCA GTG GTA TCA ACT CAA CTA CTG TTA      600
Gln Cys Thr His Gly Ile Ser Pro Val Val Ser Thr Gln Leu Leu Leu
                145                 150                 155

AAT GGT AGC CTA GCA GAA GGA GAG ATA ATA ATT AGA TCT GAA AAT CTG      648
Asn Gly Ser Leu Ala Glu Gly Glu Ile Ile Ile Arg Ser Glu Asn Leu
                160                 165                 170

ACA GAC AAT GTC AAA ACA ATA ATA GTA CAT CTT AAT CAA TCT GTA GAA      696
Thr Asp Asn Val Lys Thr Ile Ile Val His Leu Asn Gln Ser Val Glu
                175                 180                 185

GTT GTG TGT ACA AGA CCC AAC AAT AAT ACA AGA AAA AGT ATA AGG ATA      744
Val Val Cys Thr Arg Pro Asn Asn Asn Thr Arg Lys Ser Ile Arg Ile
190                 195                 200

GGA CCA GGA CAA ACA TTT TAT GCA ACA GGA GAC ATA ATA GGA GAC ATA      792
Gly Pro Gly Gln Thr Phe Tyr Ala Thr Gly Asp Ile Ile Gly Asp Ile
205                 210                 215                 220

AGA CAA GCA CAT TGT AAC ATT AGT GAA GAT AAA TGG AAT GAA ACT TTA      840
Arg Gln Ala His Cys Asn Ile Ser Glu Asp Lys Trp Asn Glu Thr Leu
                225                 230                 235

CAA AGG GTA GGT AAA AAA CTA GCA GAA CAC TTC CCT AAT AAA ACA ATA      888
Gln Arg Val Gly Lys Lys Leu Ala Glu His Phe Pro Asn Lys Thr Ile
                240                 245                 250

AAA TTT GCA GCA TCC TCA GGA GGG GAC CTA GAA ATT ACA ACA TAT AGT      936
Lys Phe Ala Ala Ser Ser Gly Gly Asp Leu Glu Ile Thr Thr Tyr Ser
                255                 260                 265

TTT AAT TGT AGA GGA GAA TTT TTC TAT TGC AAT ACA TCA GGC CTG TTC      984
Phe Asn Cys Arg Gly Glu Phe Phe Tyr Cys Asn Thr Ser Gly Leu Phe
270                 275                 280

AAT GGT ACA TAC ATG CCT AAT GGT ACA AAA AGT AAT TTA AAC TCA ACC     1032
Asn Gly Thr Tyr Met Pro Asn Gly Thr Lys Ser Asn Leu Asn Ser Thr
285                 290                 295                 300

ATC ACA ATC CCA TGC AGA ATA AAA CAA ATT GTG AAC CTG TGG CAG GAG     1080
Ile Thr Ile Pro Cys Arg Ile Lys Gln Ile Val Asn Leu Trp Gln Glu
                305                 310                 315

GTA GGA CGA GCA ATG TAT GCC CCT CCA TTT GCC AGG AAC ATA ACA TGT     1128
Val Gly Arg Ala Met Tyr Ala Pro Pro Phe Ala Arg Asn Ile Thr Cys
                320                 325                 330

AAA TCA AAT ATC ACA GGA CTA CTA TTG GTA CGT GAT GGA GGA GAA GAC     1176
Lys Ser Asn Ile Thr Gly Leu Leu Leu Val Arg Asp Gly Gly Glu Asp
                335                 340                 345

ACA AAT GAT ACA GAG ATA TTC AGT CCT GGA GGA GGA GAT ATG AGG GAC     1224
Thr Asn Asp Thr Glu Ile Phe Ser Pro Gly Gly Gly Asp Met Arg Asp
350                 355                 360

AAT TGG AGA AGT GAA TTA TAC AAA TAT AAA GTG GTA GAA ATT AAG CCA     1272
Asn Trp Arg Ser Glu Leu Tyr Lys Tyr Lys Val Val Glu Ile Lys Pro
365                 370                 375                 380
```

```
TTG GGA GTA GCA CCC ACT ACA GCA AAA AGG AGA GTG GTG GAG AGA GAA      1320
Leu Gly Val Ala Pro Thr Thr Ala Lys Arg Arg Val Val Glu Arg Glu
                385                 390                 395

AAA AGA GCA GTG GGA TTA GGA GCT GTG TTC CTT GGG TTC TTG GGA GCA      1368
Lys Arg Ala Val Gly Leu Gly Ala Val Phe Leu Gly Phe Leu Gly Ala
            400                 405                 410

GCA GGA AGC ACT ATG GGC GCG GCG TCA ATA ACG CTG ACG GTA CAG GCC      1416
Ala Gly Ser Thr Met Gly Ala Ala Ser Ile Thr Leu Thr Val Gln Ala
        415                 420                 425

AGA CAA TTA CTG TCT GGT ATA GTG CAA CAG CAA AGC AAT TTG CTG AGG      1464
Arg Gln Leu Leu Ser Gly Ile Val Gln Gln Gln Ser Asn Leu Leu Arg
    430                 435                 440

GCT ATA GAG GCG CAA CAG CAT CTG TTG CAA CTC ACG GTC TGG GGC ATT      1512
Ala Ile Glu Ala Gln Gln His Leu Leu Gln Leu Thr Val Trp Gly Ile
445                 450                 455                 460

AAG CAG CTC CAG ACA AGA GTC CTG GCT ATA GAA AGA TAC CTA AAG GAT      1560
Lys Gln Leu Gln Thr Arg Val Leu Ala Ile Glu Arg Tyr Leu Lys Asp
                465                 470                 475

CAA CAG CTC CTA GGG ATG TGG GGC TGC TCT GGA AAA CTC ATC TGC ACC      1608
Gln Gln Leu Leu Gly Met Trp Gly Cys Ser Gly Lys Leu Ile Cys Thr
            480                 485                 490

ACT GCT GTA CCT TGG AAC TCC AGT TGG AGT AAC AGA TCT CAA ACA GAT      1656
Thr Ala Val Pro Trp Asn Ser Ser Trp Ser Asn Arg Ser Gln Thr Asp
        495                 500                 505

ATT TGG GAT AAC ATG ACC TGG ATG CAG TGG GAT AGG GAA ATT AGT AAT      1704
Ile Trp Asp Asn Met Thr Trp Met Gln Trp Asp Arg Glu Ile Ser Asn
    510                 515                 520

TAC ACA AAT ACA ATA TAC AGG TTG CTT GAA GAC TCG CAA AAC CAG CAG      1752
Tyr Thr Asn Thr Ile Tyr Arg Leu Leu Glu Asp Ser Gln Asn Gln Gln
525                 530                 535                 540

GAA AGA AAT GAA AAA GAT TTA TTA GCA TTG GAC AGT TGG AAA AAT CTG      1800
Glu Arg Asn Glu Lys Asp Leu Leu Ala Leu Asp Ser Trp Lys Asn Leu
                545                 550                 555

TGG AAT TGG TTT AGC ATA ACA AAT TGG CTG TGG TAT ATA AAA ATA TTC      1848
Trp Asn Trp Phe Ser Ile Thr Asn Trp Leu Trp Tyr Ile Lys Ile Phe
            560                 565                 570

ATA ATG ATA GTA GGA GGC TTG ATA GGT TTG AGA ATA ATT TTT GCT GTG      1896
Ile Met Ile Val Gly Gly Leu Ile Gly Leu Arg Ile Ile Phe Ala Val
        575                 580                 585

CTC TCT ATA GTG AAT AGA GTT AGG CAG GGA TAC TCA CCT TTG TCG TTT      1944
Leu Ser Ile Val Asn Arg Val Arg Gln Gly Tyr Ser Pro Leu Ser Phe
    590                 595                 600

CAG ACC CT                                                           1952
Gln Thr
605
```

(2) INFORMATION FOR SEQ ID NO: 6:

(i) SEQUENCE CHARACTERISTICS:
        (A) LENGTH: 606 amino acids
        (B) TYPE: amino acid
        (D) TOPOLOGY: linear (ii) MOLECULE TYPE: protein (xi) SEQUENCE DESCRIPTION: SEQ ID NO: 6:

```
Ser Leu Trp Asp Gln Ser Leu Lys Pro Cys Val Lys Leu Thr Pro Leu
 1               5                  10                  15

Cys Val Thr Leu Glu Cys Gly Asn Val Asn Ala Thr Asn Ile Thr Asn
            20                  25                  30

Asn Gly Glu Asn Asn Pro Thr Asn Ile Thr Asn Asn Arg Glu Glu Ile
```

```
                    35                  40                  45
Lys Asn Cys Pro Phe Asn Ala Thr Thr Glu Ile Arg Asp Arg Gln Gln
            50                  55                  60
Lys Val Tyr Ala Leu Phe Tyr Arg Leu Asp Ile Val Pro Leu Asp Asn
            65                  70                  75              80
Asn Asn Asn Ser Thr Tyr Arg Leu Ile Asn Cys Asn Thr Ser Ala Ile
                        85                  90                  95
Thr Gln Ala Cys Pro Lys Val Thr Phe Asp Pro Ile Pro Ile His Tyr
                100                 105                 110
Cys Ala Pro Ala Gly Tyr Ala Ile Leu Lys Cys Asn Asn Lys Thr Phe
            115                 120                 125
Asn Gly Thr Gly Pro Cys His Asn Val Ser Thr Val Gln Cys Thr His
            130                 135                 140
Gly Ile Ser Pro Val Val Ser Thr Gln Leu Leu Leu Asn Gly Ser Leu
145                 150                 155                 160
Ala Glu Gly Glu Ile Ile Arg Ser Glu Asn Leu Thr Asp Asn Val
                        165                 170                 175
Lys Thr Ile Ile Val His Leu Asn Gln Ser Val Glu Val Val Cys Thr
                180                 185                 190
Arg Pro Asn Asn Asn Thr Arg Lys Ser Ile Arg Ile Gly Pro Gly Gln
            195                 200                 205
Thr Phe Tyr Ala Thr Gly Asp Ile Ile Gly Asp Ile Arg Gln Ala His
            210                 215                 220
Cys Asn Ile Ser Glu Asp Lys Trp Asn Glu Thr Leu Gln Arg Val Gly
225                 230                 235                 240
Lys Lys Leu Ala Glu His Phe Pro Asn Lys Thr Ile Lys Phe Ala Ala
                        245                 250                 255
Ser Ser Gly Gly Asp Leu Glu Ile Thr Thr Tyr Ser Phe Asn Cys Arg
                260                 265                 270
Gly Glu Phe Phe Tyr Cys Asn Thr Ser Gly Leu Phe Asn Gly Thr Tyr
            275                 280                 285
Met Pro Asn Gly Thr Lys Ser Asn Leu Asn Ser Thr Ile Thr Ile Pro
            290                 295                 300
Cys Arg Ile Lys Gln Ile Val Asn Leu Trp Gln Glu Val Gly Arg Ala
305                 310                 315                 320
Met Tyr Ala Pro Pro Phe Ala Arg Asn Ile Thr Cys Lys Ser Asn Ile
                        325                 330                 335
Thr Gly Leu Leu Leu Val Arg Asp Gly Gly Glu Asp Thr Asn Asp Thr
                340                 345                 350
Glu Ile Phe Ser Pro Gly Gly Gly Asp Met Arg Asp Asn Trp Arg Ser
            355                 360                 365
Glu Leu Tyr Lys Tyr Lys Val Val Glu Ile Lys Pro Leu Gly Val Ala
            370                 375                 380
Pro Thr Thr Ala Lys Arg Arg Val Val Glu Arg Glu Lys Arg Ala Val
385                 390                 395                 400
Gly Leu Gly Ala Val Phe Leu Gly Phe Leu Gly Ala Ala Gly Ser Thr
                        405                 410                 415
Met Gly Ala Ala Ser Ile Thr Leu Thr Val Gln Ala Arg Gln Leu Leu
                420                 425                 430
Ser Gly Ile Val Gln Gln Gln Ser Asn Leu Leu Arg Ala Ile Glu Ala
            435                 440                 445
Gln Gln His Leu Leu Gln Leu Thr Val Trp Gly Ile Lys Gln Leu Gln
            450                 455                 460
```

```
Thr Arg Val Leu Ala Ile Glu Arg Tyr Leu Lys Asp Gln Gln Leu Leu
465                 470                 475                 480

Gly Met Trp Gly Cys Ser Gly Lys Leu Ile Cys Thr Thr Ala Val Pro
            485                 490                 495

Trp Asn Ser Ser Trp Ser Asn Arg Ser Gln Thr Asp Ile Trp Asp Asn
            500                 505                 510

Met Thr Trp Met Gln Trp Asp Arg Glu Ile Ser Asn Tyr Thr Asn Thr
        515                 520                 525

Ile Tyr Arg Leu Leu Glu Asp Ser Gln Asn Gln Gln Glu Arg Asn Glu
    530                 535                 540

Lys Asp Leu Leu Ala Leu Asp Ser Trp Lys Asn Leu Trp Asn Trp Phe
545                 550                 555                 560

Ser Ile Thr Asn Trp Leu Trp Tyr Ile Lys Ile Phe Ile Met Ile Val
                565                 570                 575

Gly Gly Leu Ile Gly Leu Arg Ile Ile Phe Ala Val Leu Ser Ile Val
            580                 585                 590

Asn Arg Val Arg Gln Gly Tyr Ser Pro Leu Ser Phe Gln Thr
            595                 600                 605
```

(2) INFORMATION FOR SEQ ID NO: 7:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (xi) SEQUENCE DESCRIPTION: SEQ ID NO: 7:

```
Met Pro Asn Gly Thr Lys Ser Asn Ser
1               5
```

(2) INFORMATION FOR SEQ ID NO: 8:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (xi) SEQUENCE DESCRIPTION: SEQ ID NO: 8:

```
Met Pro Asn Gly Thr Lys Gly Asn Ser
1               5
```

(2) INFORMATION FOR SEQ ID NO: 9:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (xi) SEQUENCE DESCRIPTION: SEQ ID NO: 9:

```
Met Pro Asn Gly Thr Lys Ser Asn Leu
1               5
```

(2) INFORMATION FOR SEQ ID NO: 10:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO: 10:

```
Arg Asn Glu Lys Asp Leu Leu Ala Leu Asp Ser Trp Lys Asn
1               5                   10
```